US008865135B2

(12) United States Patent
Prencipe et al.

(10) Patent No.: US 8,865,135 B2
(45) Date of Patent: Oct. 21, 2014

(54) STABLE DENTIFRICE COMPOSITIONS

(75) Inventors: Michael Prencipe, West Windsor, NJ (US); Thomas J. Boyd, Metuchen, NJ (US); M. Teresa R. Carale, Houston, TX (US)

(73) Assignee: Colgate-Palmolive Company, New York, NY (US)

( * ) Notice: Subject to any disclaimer, the term of this patent is extended or adjusted under 35 U.S.C. 154(b) by 1121 days.

(21) Appl. No.: 10/875,063

(22) Filed: Jun. 23, 2004

(65) Prior Publication Data

US 2005/0031551 A1    Feb. 10, 2005

Related U.S. Application Data

(63) Continuation-in-part of application No. 10/601,474, filed on Jun. 23, 2003, now abandoned.

(51) Int. Cl.
| *A61K 8/00* | (2006.01) |
| *A61K 8/92* | (2006.01) |
| *A61K 8/49* | (2006.01) |
| *A61K 8/44* | (2006.01) |
| *A61K 8/25* | (2006.01) |
| *A61Q 11/00* | (2006.01) |

(52) U.S. Cl.
CPC .............. *A61Q 11/00* (2013.01); *A61K 8/922* (2013.01); *A61K 8/4926* (2013.01); *A61K 8/44* (2013.01); *A61K 8/25* (2013.01)
USPC .......................................................... 424/49

(58) Field of Classification Search
None
See application file for complete search history.

(56) References Cited

U.S. PATENT DOCUMENTS

| 3,151,027 A | 9/1964 | Broge et al. |
| 3,825,560 A | 7/1974 | Saito et al. |
| 4,022,881 A | 5/1977 | Hawking |
| 4,097,604 A | 6/1978 | Thiele |
| 4,098,878 A * | 7/1978 | Baines et al. .................. 424/52 |
| 4,110,083 A | 8/1978 | Benedict |
| 4,118,472 A | 10/1978 | Gaffar et al. |
| 4,157,387 A | 6/1979 | Benedict |
| 4,198,392 A | 4/1980 | Juneja |
| 4,225,579 A | 9/1980 | Kleinberg |
| 4,255,579 A | 3/1981 | Michne |
| 4,469,674 A | 9/1984 | Shah et al. |
| 4,477,428 A | 10/1984 | Sipos et al. |
| 4,499,067 A | 2/1985 | Silbering et al. |
| 4,499,068 A | 2/1985 | Silbering et al. |
| 4,567,174 A | 1/1986 | Edwards et al. |
| 4,670,592 A | 6/1987 | Eakin et al. |
| 4,695,463 A | 9/1987 | Yang et al. |
| 4,837,008 A | 6/1989 | Rudy et al. |
| 5,180,577 A | 1/1993 | Polefka et al. |
| 5,185,155 A | 2/1993 | Behan et al. |
| 5,266,306 A | 11/1993 | Ohtsuki et al. |
| 5,472,493 A | 12/1995 | Regan |
| 5,597,553 A | 1/1997 | Baffelli et al. |
| 5,695,745 A * | 12/1997 | Barton et al. .................. 424/49 |
| 5,780,015 A * | 7/1998 | Fisher et al. .................. 424/52 |
| 5,874,068 A | 2/1999 | Nair et al. |
| 5,882,631 A | 3/1999 | Suga et al. |
| 5,989,524 A * | 11/1999 | Dromard et al. .............. 424/49 |
| 6,086,648 A | 7/2000 | Rossetti et al. |
| 6,149,903 A | 11/2000 | Holt et al. |
| 6,177,096 B1 | 1/2001 | Zerbe et al. |
| 6,228,347 B1 | 5/2001 | Hersh |
| 6,290,933 B1 | 9/2001 | Durga et al. |
| 6,419,903 B1 | 7/2002 | Xu et al. |
| 6,447,758 B1 | 9/2002 | Carale et al. |
| 6,479,036 B1 * | 11/2002 | Stanier et al. ................. 424/49 |
| 6,685,921 B2 | 2/2004 | Lawlor |
| 8,287,843 B2 | 10/2012 | Boyd et al. |
| 2002/0068039 A1 | 6/2002 | Pan et al. |
| 2003/0133883 A1 | 7/2003 | Finnegan et al. |
| 2003/0206874 A1 | 11/2003 | Doyle et al. |
| 2004/0258629 A1 | 12/2004 | Boyd et al. |
| 2004/0258630 A1 | 12/2004 | Boyd et al. |
| 2004/0258631 A1 | 12/2004 | Boyd et al. |
| 2004/0258632 A1 | 12/2004 | Boyd et al. |
| 2005/0027001 A1 | 2/2005 | Boyd et al. |

FOREIGN PATENT DOCUMENTS

| EP | 0125827 | 11/1984 |
| EP | 0126558 | 11/1984 |
| EP | 0422803 | 4/1991 |
| EP | 0485616 | 5/1992 |
| FR | 2143557 | 2/1973 |
| GB | 1352420 | 5/1974 |
| GB | 1549074 | 7/1979 |
| GB | 2210264 | 6/1989 |
| HU | 176671 | 4/1981 |
| JP | 51023571 | 7/1976 |
| JP | 56009211 | 1/1981 |
| JP | 60092208 | 5/1985 |
| JP | 61056214 | 12/1986 |
| JP | H3-291211 | 12/1991 |
| JP | 04005221 | 1/1992 |
| JP | 04036230 | 2/1992 |
| JP | 06084293 | 10/1994 |
| JP | 09286712 | 11/1997 |

(Continued)

OTHER PUBLICATIONS

Tsumura, Yukako et al., "Antiplaque anticaries dentifrice compositions containing cationic microbicides" XP002309055, Nov. 4, 1997.

(Continued)

*Primary Examiner* — Snigdha Maewall

(74) *Attorney, Agent, or Firm* — Howard C. Lee

(57) ABSTRACT

A cationic-compatible inorganic particulate comprising silica substantially coated with a non-ionic surfactant, such as an ethoxylated hydrogenated hydrocarbon oil. Compositions comprising the cationic-compatible particulate and a cationic active, such as cetyl pyridinium chloride or an ethyl lauryl arginine ester, are also provided.

11 Claims, No Drawings

(56) References Cited

FOREIGN PATENT DOCUMENTS

| | | | | |
|---|---|---|---|---|
| JP | 11255629 | 9/1999 | | |
| JP | 2000256155 | 9/2000 | | |
| WO | WO 91/18585 | 12/1991 | | |
| WO | WO 97/32565 | 9/1997 | | |
| WO | WO 98/50005 | 11/1998 | | |
| WO | WO 99/13734 | 3/1999 | | |
| WO | WO 99/29289 | 6/1999 | | |
| WO | WO 99/63958 | 12/1999 | | |
| WO | WO 03/013453 | 2/2003 | | |
| WO | WO 03/013454 | 2/2003 | | |
| WO | 03037285 A1 | 5/2003 | | |
| WO | WO 03/034842 | 5/2003 | | |
| WO | WO 03/037285 | * 5/2003 | | |
| WO | WO 03/037285 A1 * | 5/2003 | ............... | A61K 7/16 |
| WO | WO 03/043593 A1 * | 5/2003 | ............... | A61K 7/22 |
| WO | WO 03/072039 | 9/2003 | | |

OTHER PUBLICATIONS

Lin, Chinling et al., "Dentrifices containing cationic microbicides and nonionic surfactants dentifrices containing cationic microbicides and nonionic surfactants" XP 002309056, Sep. 21, 1999.

Tetronic 901 Block Copolymer—Technical Bulletin, 2004, BASF, European Patent Appln. No. 04755903.4 in Notice of Opposition dated May 8, 2008.

Poloxamer 215, International Cosmetic Ingredient Dictionary and Handbook, cited in European Patent Appln. No. 04755903.4 in Notice of Opposition dated May 8, 2008.

Poloxamer 1104 Monographs, International Cosmetic Ingredient Dictionary and Handbook, cited in European Patent Appln. No. 04755903.4 in Notice of Opposition dated May 8, 2008.

PEG Soyamine 1041 Monographs, International Cosmetic Ingredient Dictionary and Handbook, cited in European Patent Appln. No. 04755903.4 in Notice of Opposition dated May 8, 2008.

Kirk-Othmer, "Encyclopedia of Chemical Technology, vol. 22, Surfactants and Detersive Systems" Wiley-Interscience, 1983, Ed. 3rd.

G.R. O'Shea Company, Vertellus™; Castor Oil and Its Chemistry, Unknown publication date.

* cited by examiner

STABLE DENTIFRICE COMPOSITIONS

CROSS-REFERENCE TO RELATED APPLICATIONS

This application is a continuation-in-part of U.S. patent application Ser. No. 10/601,474 filed on Jun. 23, 2003.

BACKGROUND

The present invention relates to an oral care composition which contains an inorganic particulate component in an oral care composition, and more particularly to a dentifrice composition containing a cationic-compatible inorganic particulate component with an oral care active antibacterial compound, which achieves plaque reduction with superior breath freshening characteristics.

Halitosis, the technical term for bad breath, or Fetor ex Oris, is an undesirable condition. As a matter of fact, everyone, excluding the very young, occasionally has bad breath, with approximately 25% suffering on a regular basis and the problem tends to get worse and more frequent as one gets older. The problem seems to be evenly split between men and women. Bad breath results when proteins from the food we eat and saliva debris are broken down by bacteria. Even the cleanest mouth hosts millions of bacteria which have the potential to decompose these protein-containing particles left in the mouth. This bacterial population forms foul smelling products, called volatile sulfur compounds (VSC)—such as hydrogen sulfide ("rotten eggs") and methyl mercaptans ("skunk smell") and other odorous and bad tasting compounds. Up to 80-90% of bad breath that originates in the mouth is by this mechanism.

Dental plaque or plaque bio-film is a soft deposit that forms on teeth and is comprised of an accumulation of bacteria and salivary as well as food by-products. Plaque adheres tenaciously at the points of irregularity or discontinuity, e.g., on rough calculus surfaces, at the gum line, on tongue surface and within crevices, and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example U.S. Pat. No. 5,874,068 and GB 1352420 disclose that arginine derivative compounds exhibit antibacterial activity when used in oral compositions such as mouthrinses to counter plaque formation by bacterial accumulation in the oral cavity. Arginine derivative compounds and their salts in particular show excellent inhibitory effect against microorganisms which possess relatively strong resistance to bacterial such as *S. aureus, S. mutans, F. nucleatum* which are involved in plaque formation on teeth. Other cationic oral care active ingredients, such as bis biguanides or cetyl pyridinium chloride (CPC) are also known for their inhibitory effect on plaque formation and bacterial accumulation in the oral cavity.

Although the cationic active material compounds, such as for example, the arginine derivative compounds disclosed in the prior art, are effective antibacterial agents, when these compounds are included in silica containing dentifrice it was discovered that when the dentifrice was applied to the teeth, the bioavailability of the arginine derivative compound was reduced to a level whereby little antiplaque benefit was achieved. Investigation of this problem led to the discovery that compounds such as abrasives and thickeners such as silica compounds conventionally used in the preparation of dentifrice compositions were the factor responsible for the impairment of the antiplaque efficacy of the arginine derivative compound.

Thus, there is a clear need in the art to formulate a dental product capable of delivering a cationic active antiplaque antibacterial agent whereby the ingredients used to prepare the dentifrice composition do no inhibit the bioavailability of the cationic antiplaque agent so that optimum antiplaque benefits result.

SUMMARY

In one aspect, the present invention provides a cationic-compatible inorganic component for an oral care composition comprising an inorganic particulate component comprising silica and having a surface substantially coated with a non-ionic surfactant to form the cationic-compatible inorganic component.

In another aspect the present invention provides an oral care composition comprising an active ingredient comprising a cationic compound and an inorganic particulate component having a surface substantially coated with a non-ionic surfactant.

In yet another aspect, the present invention provides a method of making a dentifrice having an enhanced availability of a cationic oral care active ingredient comprising coating an inorganic particulate component with a non-ionic surfactant to form a cationic-compatible inorganic component, and adding the cationic-compatible inorganic component into a dentifrice composition comprising a cationic oral care active compound.

It has been discovered that compositions and methods of this invention afford advantages over prior art oral care compositions using cationic antibacterial ingredients and inorganic particulates, such as those known in the art. Such advantages over the art include one or more of the following: enhanced bioavailability and efficacy of a cationic active ingredient translating to improved antibacterial and/or antiplaque efficacy, potential to reduce concentrations of cationic active materials in oral care compositions comprising an inorganic particulate, potential expansion of the active ingredients useful in dentifrice oral compositions. Further uses, benefits and embodiments of the present invention are apparent from the description set forth herein.

DESCRIPTION

The following definitions and non-limiting guidelines must be considered in reviewing the description of this invention set forth herein. The headings (such as "Introduction" and "Summary,") and sub-headings (such as, "Cationic Active Ingredients", "Inorganic Particulate Components", "Non-Ionic Surfactant" "Additional Antimicrobial Active Ingredients", "Dentifrice Vehicle", "Surfactants" "Thickening Agents", "Flavor Agents", "Fluoride Providing Agents", "Antitartar Agents", "Other Ingredients", and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility is made for convenience, and no inference should be drawn that the material must necessarily or solely function in accordance with its classification herein when it is used in any given composition.

The citation of any references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and any specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention, and unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As referred to herein, all compositional percentages are by weight of the total composition, unless otherwise specified.

As referred to herein, the word "substantially," when applied to a characteristic of a composition or method of this invention, indicates that there may be variation in the characteristic without having substantial effect on the chemical or physical attributes of the composition or method.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

Inorganic Particulate Components

The present invention provides cationic-compatible inorganic components for an oral care composition, said components comprising an anionic particulate substantially coated with a non-ionic surfactant. Without limiting the compositions, methods or utility of the present invention, in various embodiments, the inorganic particulate components afford diminished interaction between cationic active compounds (discussed below) and silica relative to the interaction between such materials that would occur in a prior art aqueous composition, thus optimizing the bioavailability of the cationic active compounds.

Anionic particulates among those useful herein include silica, alumina, or both. In one embodiment, the inorganic component material comprises silica. Silica abrasives useful in the practice of the present invention include silica gels and precipitated amorphous silicas. These silicas are colloidal particles/particulates having an average particle size ranging from about 3 microns to about 12 microns, and more preferably between about 5 to abut 10 microns and a pH range from 4 to 10 preferably 6 to 9 when measured as a 5% by weight slurry.

Illustrative of silica abrasives useful in the practice of the present invention are marketed under the trade designation Sylodent XWA by Davison Chemical Division of W.R. Grace & Co., Baltimore, Md. 21203. Sylodent 650 XWA, a silica hydrogel composed of particulates of colloidal silica having a water content of 29% by weight averaging from about 7 to about 10 microns in diameter.

Other inorganic component abrasives used in the practice of the present invention include precipitated silicas having a mean particle size of up to about 20 microns, such as Zeodent 115, marketed by J.M. Huber Chemicals Division, Havre de Grace, Md. 21078, or Sylodent 783 marketed by Davison Chemical Division of W.R. Grace & Company.

The silica abrasive materials may be used individually as the sole abrasive in preparing the dental composition of the present invention or in combination with other known dentifrice abrasives such as sodium metaphosphate, dihydrated dicalcium phosphate, calcined alumina. The total quantity of abrasive present in the dentifrice compositions of the present invention is at a level of from about 5% to about 60% by weight, preferably from about 10% to about 55% by weight when the dentifrice composition is a toothpaste.

Silica compounds which function as thickening agents which may be used in the practice of the present invention include colloidal silica compounds available under the trade designation Cabo-sil manufactured by Cabot Corporation and distributed by Lenape Chemical, Bound Brook, N.J.; Zeodent 165 from J.M. Huber Chemicals Division, Havre de Grace, Md.; and Sylodent 15, available from Davison Chemical Division of W.R. Grace Corporation, Baltimore, Md.

Non-Ionic Surfactant

In one aspect of the current invention, inorganic particulates that are otherwise incompatible with cationic antimicrobial agents are rendered compatible with the agents by treatment or reaction with a nonionic surfactant prior to their formulation in dentifrice compositions along with the cationic material. The improved compatibility is shown for example, from in vitro measurements of availability of the various antimicrobial agents of the compositions of the invention.

Although the invention is not to be limited by any theory of action of the non-ionic surfactant, it is believed that the reaction or treatment of the inorganic particulates with the non-ionic surfactant results in the deposition or attachment of nonionic surfactant molecules to the inorganic particulates, which results in a coating of substantially all of the charged surface of the inorganic particulates. Still not to be limited by theory, the deposition or attachment may be by either physical means, chemical means, or a combination thereof. Thus, the nonionic surfactant molecules may be held or deposited on the surface of the inorganic particulates by van der Waals attractions, hydrogen bonds, the formation of covalent bonds with reactive species on the surface of the particulates, and so on. The inorganic particulates of the present invention generally have a negative charge, and are thus considered to be anionic.

On a molecular level, surface active agents (or surfactants) are understood as being made of two moieties. The first is a hydrophilic moiety and the second is a hydrophobic moiety. As is well known, surfactants "work" by interacting with one phase of material at its surface. The resulting structure mediates the interfacial interaction of the phase with other phases. An important consideration in the action of surface active agents is the relative strength of the respective hydrophilic and hydrophobic portions of the molecule. The relative strength can be expressed and understood as a balance between the hydrophilic characteristics of one part of the molecule and the hydrophobic characteristics of another.

Nonionic surfactants are made of chemical constituents that result in a molecule having no ionic charges. As such, the nonionic surfactant are distinguished from cationic surfactants, anionic surfactants, and amphoteric surfactants. In a preferred embodiment, the hydrophilic moiety of a nonionic surfactant is based on a polyoxyalkylene structure. A polyoxyalkylene structure is a polyether type polymer that formally represents the polymerization product of a wide variety of cyclic ethers that polymerize by ring opening polymerization. Non-ionic surfactants useful in the invention are usually synthesized by the polymerization of such cyclic ethers.

Among the cyclic ethers that may be polymerized to form the hydrophilic portion of the nonionic surfactant of the invention are those having from two to eight carbon atoms, with ring structures of three to five atoms. Suitable cyclic ether systems for polymerization include oxiranes (three membered rings), oxetanes (four member rings), and furans (five-membered rings). The surfactants may be made by homo or copolymerization of one or more of such cyclic ethers. In a preferred embodiment, oxiranes are polymerized under basic catalysis, followed by neutralization of the polymeric product. Polyoxyalkylene or polyether hydrophilic moieties may also be produced by acid catalyzed polymerization of cyclic ethers.

The size and relative proportion of alkylene groups in the polyoxyalkylene hydrophilic moiety determines its relative hydrophilic nature. In general the hydrophilic nature is the related to the proportion of lower cyclic ethers that are present in the polymerization mix. In a preferred embodiment, the polyoxyalkylene hydrophilic moiety of the surfactant is made of polyoxyethylene, resulting from the polymerization of ethylene oxide. (Ethylene oxide is an oxirane containing two carbons). Relatively smaller amounts of propyleneoxide, butyleneoxide, and other higher cyclic ethers may be copolymerized with the ethylene oxide to form the hydrophilic moieties on the surfactant of the invention, as long as the balance of hydrophilic and hydrophobic character in the resulting surfactant is suitable for application in the invention.

The hydrophobic moieties on the non ionic surfactants of the invention are generally organic radicals containing at least about twelve carbons. These surfactants are made by polymerizing ethylene oxide or a mixture of alkylene oxides and/or cyclic ethers onto an organic molecule that serves as a starting material. The starting material contains at least about 12 carbon atoms, and an organic group containing an active hydrogen that will react with the cyclic ethers to form the polyoxyalkylene. Reactive organic groups containing active hydrogen include without limitation, hydroxyl, carboxyl, amine, amide, and mercaptan. A preferred reactive group is hydroxyl, whereby the starting material is an organic alcohol containing at least about 12 carbon atoms. Thus, suitable nonionic surfactants may be prepared by polymerizing ethylene oxide or a mixture of cyclic ethers onto fatty alcohols, fatty acids, fatty acid amides, and the like. Commercially available fatty alcohols, fatty acids, fatty amides and fatty amines includes those containing from about 12 to about 26 carbon atoms.

In a preferred embodiment, the hydrophobic moiety is based on hydroxyl functional diglycerides and triglycerides. Such diglycerides and triglycerides are available as vegetable oils. In a preferred embodiment, castor oil, a triglyceride containing hydroxyl functionality is used to make the non-ionic surfactants of the invention. In a preferred embodiment, ethyleneoxide or a mixture of cyclic ethers is polymerized onto castor oil until at least about 10, preferably about 20, and more preferably about 40 alkylene oxide units are added per molecule of the oil. Preferably, the extent of alkoxylation is less than 600, preferably less than 400, and more preferably less than 200. The castor oil alkoxylate resulting from the polymerization may then be hydrogenated by conventional means to form a hydrogenated castor oil alkoxylate. Alternatively, the castor oil, which in its native form contains olefinic unsaturation, may be hydrogenated prior to the reaction of the hydroxyl functional oil with the cyclic ethers. Thus, in a preferred embodiment, the nonionic surfactant comprises a castor oil alkoxylate or a hydrogenated alkoxylate having from about 20 to 200 repeating oxyalkylene units in the hydrophilic moiety. In a preferred embodiment, the oxyalkylene units are predominantly oxyethylene. In a particularly preferred embodiment, the polyoxyalkylene moiety is polyoxyethylene.

Ethoxylated castor oil and hydrogenated ethoxylated castor oils are known by the non-proprietary name of PEG hydrogenated castor oils, in accordance with dictionary of the Cosmetics, Toiletries and Fragrance Association, 3rd Edition which name is used in conjunction with a numeric suffix to designate the degree of ethoxylation of the hydrogenated castor oil product, i.e., the number of moles of ethylene oxide added to the hydrogenated castor oil product. Such ethoxylated and hydrogenated ethoxylated castor oils are commercially available and are commonly designated as PEG NN castor oil or PEG NN hydrogenated castor oil, where NN designates the number of ethylene oxide units polymerized onto the castor oil to form the non-ionic surfactant. Suitable PEG hydrogenated castor oils include, PEG 16, 20, 25, 30, 40, 50, 60, 80, 100, and 200. In a preferred embodiment, the non-ionic surfactant is a PEG 40 hydrogenated castor oil commercially available under the trade name Cremophor RH40, a commercially available product from BASF-Wyandotte, Parsippany, N.J. In certain embodiments, the hydrogenated castor oils used to treat the inorganic compound particulates prior to their incorporation into the dentifrice of the present invention, are prepared by hydrogenating castor oil and treating the hydrogenated product with from about 10 to about 200 moles of ethylene glycol. Ethoxylated hydrogenated castor oil is coated on the silica compounds used in the preparation of the compositions of the present invention at a castor oil to silica weight ratio of about 1:10 to 1:2.

Cationic Active Ingredients

The present invention provides compositions comprising a cationic active ingredient. As referred to herein, such ingredients include any material comprising a cationic (positively charged) moiety as present in a composition of this invention. In various embodiments, a cationic active ingredient is one, which if in an aqueous composition, would be reactive with an anionic dentifrice component (e.g., silica abrasive). (It should be understood, without limiting the compositions, methods or utility of the present invention, that the reactivity of such cationic active ingredients with an anionic component is reduced or eliminated in the compositions of the present invention.)

Cationic active ingredients among those useful herein include materials operable to treat or prevent a disorder or provide a cosmetic benefit. In various embodiments, the active is a "systemic active" which is operable to treat or prevent a disorder which, in whole or in part, is not a disorder of the oral cavity. In various embodiments, the active is an "oral care active" operable to treat or prevent a disorder or provide a cosmetic benefit within the oral cavity (e.g., to the teeth, gingival or other hard or soft tissue of the oral cavity). Oral care actives among those useful herein include whitening agents, anticaries agents, tartar control agents, antiplaque agents, periodontal actives, abrasives, breath freshening agents, malodor control agents, tooth desensitizers, salivary stimulants, and combinations thereof. It is understood that while general attributes of each of the above categories of actives may differ, there may some common attributes and any given material may serve multiple purposes within two or more of such categories of actives.

In one embodiment, the cationic active material has an antibacterial or antiattachment benefit. Suitable cationic antibacterial agents for use in oral compositions of the invention include, for example:

(i) quaternary ammonium compounds, such as those in which one or two of the substituents on the quaternary nitrogen has from 8 to 20, preferably from 10 to 18 carbon atoms and is preferably an alkyl group, which may optionally be interrupted by an amide, ester, oxygen, sulfur, or heterocyclic ring, while the remaining substituents have a lower number of carbon atoms, for instance from 1 to 7, and are preferably alkyl, for instance methyl or ethyl, or benzyl. Examples of such compounds include benzalkonium chloride, dodecyl trimethyl ammonium chloride, benzyl dimethyl stearyl ammonium chloride, hexadecyltrimethyl ammonium bromide, benzethonium chloride (diisobutyl phenoxyethoxyethyl dimethyl benzyl ammonium chloride) and methyl benzethonium chloride;

(ii) pyridinium and isoquinolinium compounds, including hexadecylpyridinium chloride and alkyl isoquinolinium bromides;

(iii) pyrimidine derivatives such as hexetidine (5-amino-1,3-bis(2-ethylhexyl)-5-methyl-hexahydropyrimidine);

(iv) amidine derivatives such as hexamidine isethionate (4,4'-diamidino-αω-diphenoxy-hexane isethionate);

v) bispyridine derivatives such as octenidine dihydrochioride (N,N'[1,10-decanediyldi-1(4H)-pyridinyl-4-ylidene]-bis(1-octanamine)dihydrochloride);

(vi) guanides, for example, mono-biguanides such as p-chlorobenzyl-biguanide and N'(4-chlorobenzyl)-N"-(2,4-dichlorobenzyl) biguanide, poly(biguanides) such as polyhexamethylene biguanide hydrochloride, and bis-biguanides of the general formula (1):

nucleus; and orally acceptable acid addition salts thereof; examples of such bis-biguanides include chlorhexidine and alexidine. Suitable acid addition salts of the bis-biguanides of general formula (1) include the diacetate, the dihydrochioride and the digluconate. Suitable acid addition salts of chlorhexidine are those which have a water solubility at 20° C. of at least 0.005% w/v and include the digluconate, diformate, diacetate, dipropionate, dihydrochloride, dihydroiodide, dilactate, dinitrate, sulphate, and tartrate salts. Preferably the salt is the dihydrochloride, diacetate or digluconate salt of chlorhexidine. Suitable acid addition salts of alexidine include the dihydrofluoride and the dihydrochloride salts; and vii) $N^{\alpha}$-acyl amino acid alkyl esters and salts generally represented by the formula (2) below:

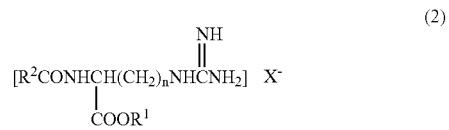

where $R^1$ is an alkyl chain of 1 to 8 carbon atoms, preferably from 1 to 3 carbon atoms, and most preferably 3 carbon atoms; $R^2$ is an alkyl chain of 6 to 30 carbon atoms, preferably from 10 to 12 carbon atoms, and mixtures thereof; and X is an anion. In various embodiments, the $R^2CO$ moiety comprises a natural fatty acid residue such as a natural fatty acid selected from the group consisting of coconut oil fatty acid, tallow fatty acid residue, or a mono-fatty acid residue such as selected from the group consisting of lauroyl ($C_{12}$), myristyl ($C_{14}$), stearoyl ($C_{18}$) fatty acid residues, and mixtures thereof. In one embodiment, the $R^2CO$ moiety comprises a lauroyl fatty acid residue.

X may be any counter-anion that provides a reasonable degree of solubility in water (preferably at least about 1 g in 1 L of water). Examples of X counter anions which form antibacterial ester salts of the above identified formula, include inorganic acid salts, such as those comprising halogen atoms (e.g., chloride or bromide) or dihydrogen phosphate, or an organic salt such as acetate, tautarate, citrate, or pyrrolidone-carboxylate (PCA). The chloride salt is preferred.

Examples of antibacterial ester compounds preferred in the practice of the present invention are antibacterial ester compound of the above-identified formula wherein n in the formula equals 3 useful in the practice of the present invention include N'-cocoyl-L-arginine methyl ester, $N^{\alpha}$-cocoyl-L-arginine ethyl ester, $N^{\alpha}$-cocoyl-L-arginine propyl ester, $N^{\alpha}$-stearoyl-L-arginine methyl ester, $N^{\alpha}$-stearoyl-L-arginine ethyl ester hydrochloride. The term 'cocoyl" is an abbreviation for coconut oil fatty acid residue, and chloride salts of

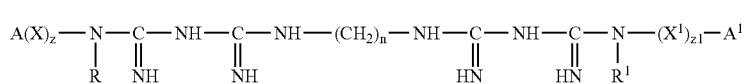

in which A and $A^1$ each represent (i) a phenyl group optionally substituted by ($C_{1-4}$) alkyl, ($C_{1-4}$) alkoxy, nitro, or halogen, (ii) a ($C_{1-12}$) alkyl group, or (iii) a ($C_{4-12}$) alicyclic group; X and $X^1$ each represent ($C_{1-3}$) alkylene; R and $R^1$ each represent hydrogen, ($C_{1-12}$) alkyl, or aryl ($C_{1-6}$) alkyl; Z and Z1 are each 0 or 1; n is an integer from 2 to 12; and the polymethylene chain $(CH_2)_n$ may optionally be interrupted by oxygen or sulfur or an aromatic (for instance phenyl or naphthyl)

these compounds, these ester compounds and the salts thereof being referred to in this specification as arginine derivative compounds. In one embodiment, the arginine derivative compound is the hydrogen chloride salt of ethyl lauroyl arginine.

Advantageously, the cationic antibacterial agent is present in the range 0.005 to 10 per cent, preferably 0.005 to 5 per cent, more preferably 0.005 to 2.5 per cent by weight of the oral composition.

Oral Care Compositions

The present invention provides oral care compositions comprising:
(a) an active ingredient comprising a cationic compound; and
(b) an inorganic particulate component having a surface substantially coated with a non-ionic surfactant that diminishes chemical interaction between the cationic compound and the inorganic component. Such compositions preferably comprise an orally-acceptable carrier.

In one embodiment, the composition is a dentifrice.

In various embodiments, the orally-acceptable dentifrice vehicle used to prepare the dentifrice composition comprises a water-phase. The compositions of the present invention optionally include other materials such as adhesion agents, viscosity modifiers, diluents, surfactants, foam modulators, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with the cationic active material and other ingredients of the composition.

The compositions of the present invention preferably comprising a humectant. The humectant is preferably glycerin, sorbitol, xylitol, and/or propylene glycol of molecular weight in the range of 200 to 1,000. Other humectants, such as polyethylene glycol, and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 15 to 30% by weight of the oral composition. Water employed in the preparation of commercially suitable toothpastes should preferably be deionized and free of organic impurities. These amounts of water include the free water which is added plus-that which is introduced with other materials such as with sorbitol.

Surfactants useful in the practice of the present invention include nonionic, zwitterionic, and anionic surfactants. Suitable nonionic surfactants useful in the present invention include condensates of sorbitan esters of fatty acids with ethylene oxide (polysorbates) such as sorbitan mono-oleate with from about 20 to about 60 moles of ethylene oxide (e.g., "Tweens", a trademark of ICI US, Inc.). Particularly preferred Polysorbates are Polysorbate 20 (polyoxyethylene 20 sorbitan monolaurate, Tween 20) and Polysorbate 80 (polyoxyethylene 20 sorbitan mono-oleate, Tween 80). Other nonionic surfactants include poly(oxyethylene)-poly(ox propylene) block copolymers. Such copolymers are known commercially by the non-proprietary name of poloxamers, which name is used in conjunction with a numeric suffix to designate the individual identification of each copolymer. Poloxamers may have varying contents of ethylene oxide and propylene oxide which results in poloxamers which have a wide range of chemical structures and molecular weights. A preferred pole-axes is Poloxamer 407, sold under the trade name Pluronic F-127 by BASF, Wyandotte, Parsippany, N.J.

Zwitterions surfactants useful in the practice of the present invention particularly betaine surfactants, include surfactants disclosed in U.S. Pat. No. 5,180,577 incorporated herein by reference. Typical alkyl diethyl betaines include decal betaine 2-(N-decyl-N,N-dimethylammonio)acetate, cocobetaine or 2-(N-coc-N, N-dimethyl ammonio)acetate, myristyl betaine, palmityl betaine, lauryl, betaine, cetyl betaine, cetyl betaine, stearyl betaine, etc. The amido betaines are exemplified by cocoamidoethyl betaine, cocoamidopropyl betaine, lauramidopropyl betaine and the like. The preferred betaine is the cocoamidopropyl betaine.

In the present invention, non-ionic and zwitterionic surfactants are particularly preferred. However, anionic surfactants, where compatibilized with the cationic active ingredient compounds, may also be useful, and include such surfactants as: water soluble salts of higher fatty acid monoglyceride monosulfates, sodium salts of the monosulfated monoglycerides, or hydrogenated coconut oil fatty acids, higher alkyl-sulfates, such as sodium lauryl sulfate and alkyl aryl sulfonates, such as sodium dodecyl benzene sulfonate. Other surfactants such as fluorinated surfactants and surface tension reducing materials may also be incorporated within the compositions.

The surfactant(s) is present in the oral composition of the present invention in the range from about 0.1% to about 5% by weight preferably from about 0.6% to about 2.0% by weight.

Thickeners used in the compositions of the present invention other than silica thickeners include natural and synthetic gums and colloids. Suitable thickeners include naturally occurring polymers such as carrageenans, xanthan gum, synthetic thickener such as polyglycols of varying molecular weights sold under the tradename Polyox and cellulose polymers such as hydroxyethyl cellulose and hydroxypropyl cellulose. Other inorganic thickeners include natural and synthetic clays such as hectorite clays, lithium magnesium silicate (laponite) and magnesium aluminum silicate (Vee-gum).

The thickening agent is present in the dentifrice composition in amounts of about 0.1 to about 10% by weight, preferably about 0.5 to about 4.0% by weight.

The dentifrice composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the dentifrice composition at a concentration of about 0.1 to about 5% by weight and preferably about 0.5 to about 1.5% by weight.

The compositions of the present invention optionally comprise an additional active material, which is operable for the prevention or treatment of a condition or disorder of hard or soft tissue of the oral cavity, the prevention or treatment of a physiological disorder or condition, or to provide a cosmetic benefit. In various embodiments, the active is a "systemic active" which is operable to treat or prevent a disorder which, in whole or in part, is not a disorder of the oral cavity. In various embodiments, the active is an "oral care active" operable to treat or prevent a disorder or provide a cosmetic benefit within the oral cavity (e.g., to the teeth, gingival, or other hard or soft tissue of the oral cavity). Oral care actives among those useful herein include whitening agents, anticaries agents, tartar control agents, antiplaque agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives. Preferably, such actives are selected for compatibility with the cationic active material and with other ingredients of the composition. Actives among those useful herein are disclosed in U.S. Patent Publication 2003/0206874, Doyle et al., published Nov. 6, 2003; U.S. Pat. No. 6,290,933, Durga et al., issued Sep. 18, 2001; and U.S. Pat. No. 6,685,921, Lawlor, issued Feb. 3, 2004.

In one embodiment, the compositions comprise additional non-cationic antibacterial agents. Such antibacterial agents include those based on phenolic and bisphenolic compounds, such as, halogenated diphenyl ethers, including Triclosan (2,4,4'-trichloro-2'-hydroxy-diphenylether, triclocarban (3,4, 4-trichlorocarbanilid), as well as 2-phenoxyethanol, benzoate esters, and carbanilides. Such additional antibacterial agents can be present in the oral care composition at quantities of from about 0.01 to about 5% by weight of the oral composition.

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, ammonium fluoro silicate, as well as tin fluorides, such as stannous fluoride and stannous chloride. Sodium fluoride is preferred.

In addition to fluoride compounds, there may also be included antitartar agents such as zinc salts including zinc chloride, zinc citrate and zinc gluconate which are compatible with the antibacterial ester. These antitartar agents are included in the dentifrice composition at a concentration of about 1 to about 5% by weight.

Other agents compatible with antibacterial esters also be included in the oral composition of the present invention such as antitartar agents as for example cationic polyphosphonates such as water soluble quaternary aminoalkylene phosphonic compounds as disclosed in U.S. Pat. No. 4,118,472, the disclosure of which is herein incorporated by reference. These antitartar agents may be included in the oral composition of the present invention at a concentration of about 0.1 to about 5% by weight.

Antitartar agents which are generally recognized as not being compatible with antibacterial esters, such as pyrophosphate and polyphosphate salts, may be included in one component of a dual component oral composition system in which a first component contains the antibacterial ester and the second component contains the incompatible antitartar salt, the first and second components being maintained separate from each other until dispersed and combined for application to the teeth. Alternatively, such non-compatible antitartar agents may also be included in a single phase dentifrice composition by compatibilization techniques recognized by one of skill in the art, such as providing a low concentration of water to physically separate and prevent diffusion of the non-compatible ingredients thus diminishing contact between them.

Various other materials may be incorporated in the dentifrice compositions of this invention, including desensitizers, such as potassium nitrate; whitening agents; preservatives; silicones; and chlorophyll compounds. These additives, when present, are incorporated in the dentifrice composition in amounts which do not substantially adversely affect the properties and characteristics desired.

Methods

In one embodiment, the present invention provides a method of making a dentifrice having an enhanced availability of a cationic oral care active ingredient comprising coating an anionic inorganic component with a non-ionic surfactant to form a cationic-compatible inorganic component. The cationic-compatible inorganic component is added into a dentifrice composition comprising a cationic oral care active compound.

The preparation of dentifrices is well known in the art. More specifically, to prepare a dentifrice of the present invention, generally the humectants e.g., glycerin, sorbitol, propylene glycol, are dispersed in water in a conventional mixer under agitation. Into the dispersion are added the arginine derivative compound, organic thickeners, such as carageenan, any salts, such as sodium fluoride anticaries agents; and any sweeteners. The resultant mixture is agitated until a homogeneous gel phase is formed. Into the gel phase are added a pigment such as $TiO_2$, and any acid or base required to adjust the pH to 6 to 7. These ingredients are mixed until a homogenous phase is obtained. The mixture is then transferred to a high speed vacuum mixer; wherein, the surfactant ingredients are added to the mixture as well as the silica compounds such as silica abrasive Zeodent 115 and silica thickener Zeodent 165 both compounds being precoated with an ethoxylated hydrogenated castor oil. The mixture is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

The following example further describes and demonstrates preferred embodiments within the scope of the present invention.

Example 1

A toothpaste composition containing ethyl lauroyl arginine HCl (ELAH) and a ethoxylated hydrogenated castor oil precoated coated silica inorganic component and thickener is prepared having the following ingredients:

TABLE I

| Composition (Wt. %) Ingredients | |
|---|---|
| Polyethylene glycol 600 | 3 |
| PEG-40 castor oil | 6 |
| Hydroxyethylcellulose | 1.0 |
| Xanthan | 0.2 |
| Sodium saccharin | 0.35 |
| Sodium fluoride | 0.243 |
| Sorbitol | 40 |
| Sodium hydroxide, 50% soln. | 0.5 |
| Titanium dioxide | 0.5 |
| ELAH | 0.5 |
| Zeodent 115 | 5 |
| Zeodent 165 | 2 |
| SylodentXWA 650 | 15 |
| Polysorbate20 | 1 |
| Cocomidopropyl betaine | 1 |
| Flavor | 0.72 |
| Water to make | 100 |

The dentifrice is prepared by dispersing the sorbitol in the water in a conventional mixer under agitation. Into the dispersion is added the xanthan, PEG 40 castor oil, sodium fluoride, hydroxyethyl cellulose, and sodium saccharin. The resultant mixture is agitated until a homogeneous gel phase was formed. Into the gel phase are added $TiO_2$ and sodium hydroxide to adjust the pH to 6.5. These ingredients are mixed until a homogenous phase was obtained. The mixture is then transferred to a high speed/vacuum mixer; wherein the PEG 40 castor oil coated silica compounds Zeodent 115, Zeodent 165, and Sylodent XWA 650 are added and the mixture mixed at high speed for 25 minutes, under vacuum from about 30 mm Hg. Finally, polysorbate 20, cocoamidobetaine, flavor and ELAH are added to the mixture and mixed for an additional 10 minutes. The resultant product is a homogeneous, semisolid, extrudable paste or gel product.

The example and other embodiments described herein are exemplary and not intended to be limiting in describing the full scope of compositions and methods of this invention. Equivalent changes, modifications and variations of specific embodiments, materials, compositions and methods may be made with substantially similar results.

What is claimed is:

1. A dentifrice composition comprising:
a safe and effective amount of cationic oral care active ingredient and an anionic particulate selected from the group consisting of silica, alumina and mixtures thereof, which is coated with a non-ionic surfactant comprising an ethoxylated hydrogenated hydrocarbon oil;
wherein the cationic oral active ingredient is a $N^{\alpha}$-acyl amino acid alkyl ester, represented by the formula (2) shown below:

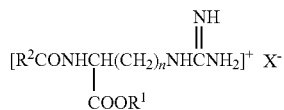

wherein $R^1$ is an alkyl chain of 1 to 8 carbon atoms; $R^2$ is an alkyl chain of 6 to 30 carbon atoms, and mixtures thereof; and $X^-$ is an anion, and n is an integer 3.

2. The composition according to claim 1, wherein said cationic oral care active ingredient is an ethyl lauroyl arginine ester or an orally acceptable salt thereof.

3. The composition according to claim 2, wherein said oral care active ingredient is ethyl lauroyl arginine hydrochloride.

4. The composition according to claim 3, wherein said ethoxylated hydrogenated hydrocarbon oil is ethoxylated hydrogenated castor oil.

5. The composition according to claim 1, wherein said composition is a single-component composition.

6. The composition of claim 2, wherein the anionic particulate is a silica selected from the group consisting of silica gels, precipitated amorphous silicas and mixtures thereof.

7. The composition of claim 4, wherein the anionic particulate is a silica selected from the group consisting of silica gels, precipitated amorphous silicas and mixtures thereof.

8. The composition of claim 5, wherein the anionic particulate is a silica selected from the group consisting of silica gels, precipitated amorphous silicas and mixtures thereof.

9. The composition of claim 6, wherein the compositions further comprises an anti-tartar agent selected from the group consisting of a zinc salt, a pyrophosphate salt, a polyphosphate salt and mixtures thereof.

10. The composition of claim 7, wherein the compositions further comprises an anti-tartar agent selected from the group consisting of a zinc salt, a pyrophosphate salt, a polyphosphate salt and mixtures thereof.

11. The composition of claim 8, wherein the compositions further comprises an anti-tartar agent selected from the group consisting of a zinc salt, a pyrophosphate salt, a polyphosphate salt and mixtures thereof.

* * * * *